United States Patent [19]

Yamamoto et al.

[11] Patent Number: 4,622,971

[45] Date of Patent: Nov. 18, 1986

[54] ERRONEOUS IMPINGEMENT PROTECTIVE DEVICE FOR LASER SYSTEM

[75] Inventors: Takashi Yamamoto; Akira Ishimori, both of Amagasaki, Japan

[73] Assignee: Mitsubishi Denki Kabushiki Kaisha, Tokyo, Japan

[21] Appl. No.: 734,830

[22] Filed: May 17, 1985

Related U.S. Application Data

[63] Continuation of Ser. No. 453,569, Dec. 27, 1982, abandoned.

[30] Foreign Application Priority Data

Dec. 28, 1981 [JP] Japan .................................. 56-215818
Feb. 19, 1982 [JP] Japan .................................. 57-26609

[51] Int. Cl.$^4$ ................................................ A61N 3/00
[52] U.S. Cl. ............................. 128/395; 219/121 LA
[58] Field of Search .................................. 128/4–8, 128/303.1, 395–398, 633; 219/121 L, 121 LA, 121 LB, 121 LU, 121 LV, 121 LX; 350/96.25, 96.26

[56] References Cited

U.S. PATENT DOCUMENTS

| | | | |
|---|---|---|---|
| 3,123,066 | 3/1964 | Brunley | 128/397 |
| 3,329,818 | 7/1967 | Woehl | 350/96.25 |
| 3,595,220 | 7/1971 | Kawahara | 128/6 |
| 4,213,704 | 7/1980 | Burns et al. | 219/121 L |
| 4,266,549 | 5/1981 | Kimura | 128/303.1 |
| 4,273,111 | 6/1981 | Tsukaya | 128/6 |
| 4,438,705 | 3/1984 | Wilinsky | 128/303.1 |

Primary Examiner—Edward M. Coven
Assistant Examiner—Max F. Hindenburg
Attorney, Agent, or Firm—Sughrue, Mion, Zinn, Macpeak and Seas

[57] ABSTRACT

A plurality of light detector pairs are spaced around the emitter end of a surgical laser handpiece with different, converging directivities to sense pilot beam reflections from a target. Their differentially compared outputs are applied to a distance determining unit having an adjustable threshold or majority decision level to detect when the end of the handpiece is at a desired distance from the target, whereupon the main laser beam is activated. Such a majority distance determination reduces activation errors due to the reflective characteristics and contours of the target surface and the angle of the handpiece.

3 Claims, 14 Drawing Figures

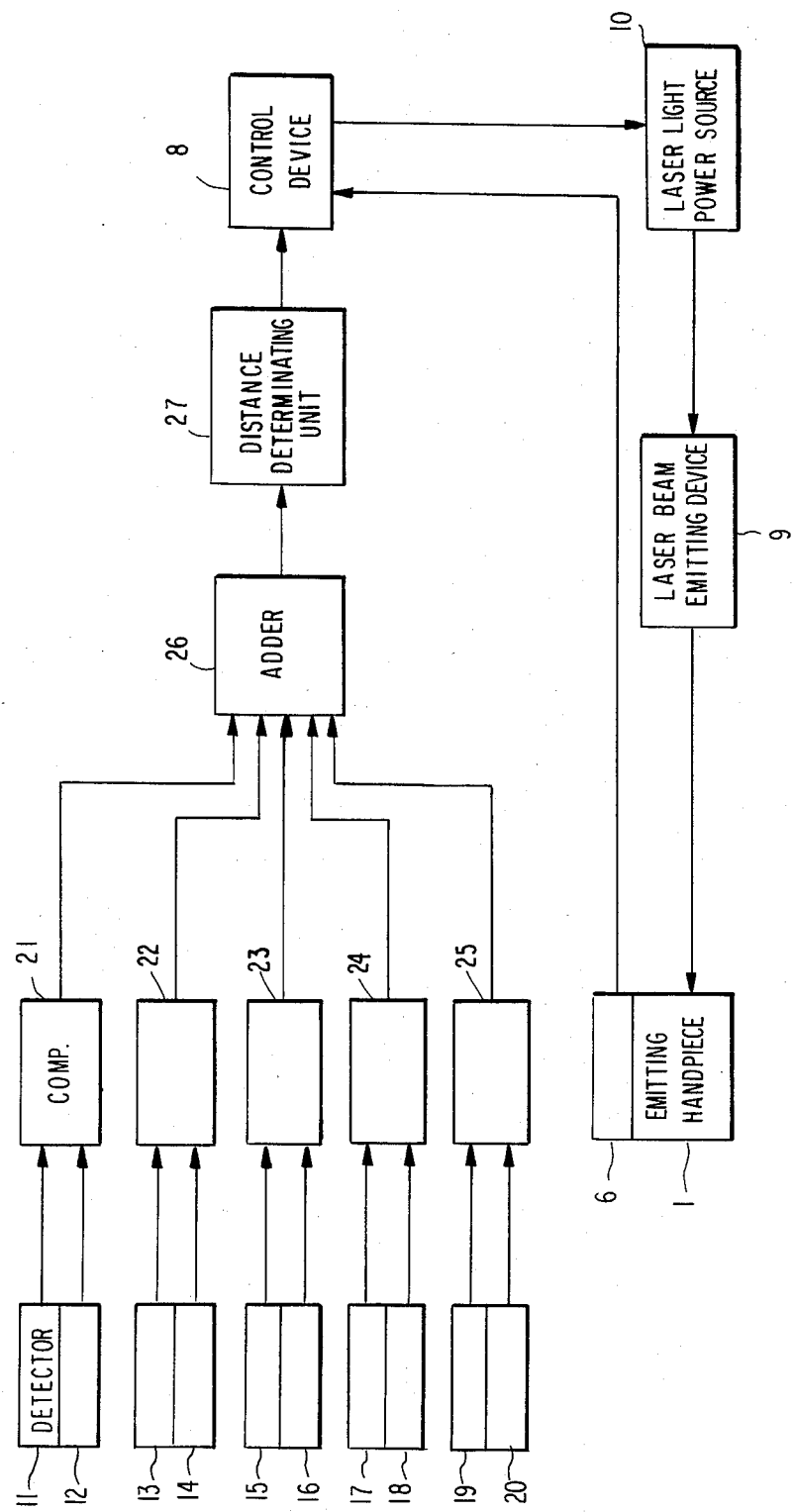

FIG. II
PRIOR ART

ERRONEOUS IMPINGEMENT PROTECTIVE DEVICE FOR LASER SYSTEM

This is a continuation, of application Ser. No. 453,569 filed Dec. 27, 1982, abandoned May 17, 1985.

BACKGROUND OF THE INVENTION

1. Field of the Invention

The present invention relates to an erroneous impingement protective device for a laser system. The device is arranged such that the operational length of the laser beam is limited to lie within a predetermined range to prevent the erroneous impingement of the beam caused by manipulating errors or operational faults. The generation of the laser beam is thus enabled only within a control range at a predetermined distance in the direction of the emitted beam from the end of the beam emitting handpiece.

2. Description of the Prior Art

A conventional protective device for a surgical laser is disclosed in "Lasers in Surgery and Medicine" Volume 1, Number 1, 1980. FIGS. 1 and 3 illustrate such a device. A laser beam emitting handpiece 1 is provided with a pair of light detectors 2,3 incorporated within pipes or tubes having fixed directive angles as shown. A visible beam 4 of axial laser light, such as from a helium-neon pilot source, is directed through the emitter end of the handpiece to a target 5, and the reflected and diffused light is sensed by the two light detectors 2,3.

FIG. 2 illustrates the output characteristics of the detectors for different targets; $A_0$, $A_1$ and $A_2$ represent the distance-output characteristics of the light detector 2, and $B_0$, $B_1$ and $B_2$ represent those of the light detector 3. Although the curves of these characteristics vary depending upon the reflection factors and inclinations of the target, there is substantially no change in the crossing points of the characteristic curves of the two detectors. Accordingly, the differential output of the two detectors lies at a substantially constant point even for different targets. By utilizing the distance corresponding to such crossover as a reference point, invisible surgical laser light, such as from a $CO_2$ source, may be emitted or blocked whenever a predetermined distance range flanking such reference point is detected.

The conventional protective device having a pair of light detectors 2,3 is arranged, as shown in FIG. 3, such that a distance defining element 7, such as a differential comparator, serves to determine whether the differential value between the two detector outputs lies in the ON region or OFF region flanking the crossover point. A laser control unit 8 is adapted to control a laser power source 10 and surgical laser emitting unit 9 on the basis of the differential comparison, whereby the surgical laser beam is emitted only when the switch 6 on the handpiece is turned on by the operator and the target is present within the ON region. The pilot beam 4 always remains on, of course, when the system is in use; it is energized by a separate power source, not shown.

In order to make the operation of the system understood more clearly, flow charts for two types of conventional surgical laser systems are shown in FIG. 11 and FIG. 12. At step I in FIG. 11 a main switch is turned on, which starts the pilot laser oscillator emitting a beam as well as the monitoring of the distance between the handpiece and the target. After the power of the main laser beam and the emitting period are set at step III and the preparing switch for emitting the main laser beam is turned on at step IV, the main laser oscillator starts operating at step V. A hand or foot operated switch for emitting the main laser beam is next turned on at step VI, whereafter the distance between the handpiece and the target to which the pilot laser beam has been emitted is determined at step VII. If the distance is in the ON region a blocking shutter which has prevented the main laser from being emitted is withdrawn at step VIII and the surgery begins. After the surgical operation is finished, the switch for emitting the main laser beam is turned off at step IX, and the shutter is then closed to prevent the main laser beam from being emitted at step X.

Another sequence is shown in FIG. 12, wherein steps I to IV are identical to those in FIG. 11. After step IV the hand or foot switch for emitting the main laser beam is turned on at step V, and the distance between the handpiece and the target is then determined at step VI. If appropriate, the main laser oscillator starts and the main laser beam is emitted at step VII. After the surgical operation is finished the switch for emitting the main laser beam is turned off at step VIII, and the main laser oscillator stops working at step IX.

In the conventional system, the light detectors are oriented toward the reflected pilot beam from only one angle or direction on one side of the handpiece, whereas the handpiece may be aimed and manipulated relative to the living target or body from a number of different directions due to the irregular surface of the target, whereby the system tends to be unstable. Furthermore, a system of this type has the drawback that unstable operations will occur for targets having a higher than normal reflection factor since the structure of the system has been designed for intended use with diffuse reflections. As may be seen from FIGS. 4 and 5 showing the measurement of the reflection components from targets such as a ham and a beef liver, respectively, the ham surface produces a substantial amount of diffuse reflection components, while the beef surface produces more regular reflection components forming a sharp, high amplitude peak extending in one direction (at 90° in this case). Thus, if only such sharp or regular reflection components are received by one of the two detectors, the resulting distance determination will be erroneous. Moreover, changes in the contour of the target surface when incised by the surgical laser will also lead to instabilities in the distance control operation.

SUMMARY OF THE INVENTION

The present invention obviates the disadvantages of the conventional systems by providing a laser light erroneous impingement protective device comprising a plurality of pairs of light detectors or light pipes having different directivities, each pair or each group consisting of the predetermined number of the pairs thereof conducting a local distance measurement. The system functions in a stable manner for any regular reflection components and variable contours of the target surface by detecting or indicating the ON region only when a certain number of pairs or groups have differential outputs which exceed a predetermined threshold or decision level.

BRIEF DESCRIPTION OF THE DRAWINGS

The present invention will become more readily apparent from the following detailed description taken in conjunction with the accompanying drawings in which:

FIG. 7 is a block diagram of a protective system embodying the detector arrangement shown in FIG. 6, FIGS. 8(a) and 8(b) show sectional side views of light detectors according to other embodiments of the invention, formed with fiber and directional plates.

DETAILED DESCRIPTION OF THE PREFERRED EMBODIMENTS

Figure 11:
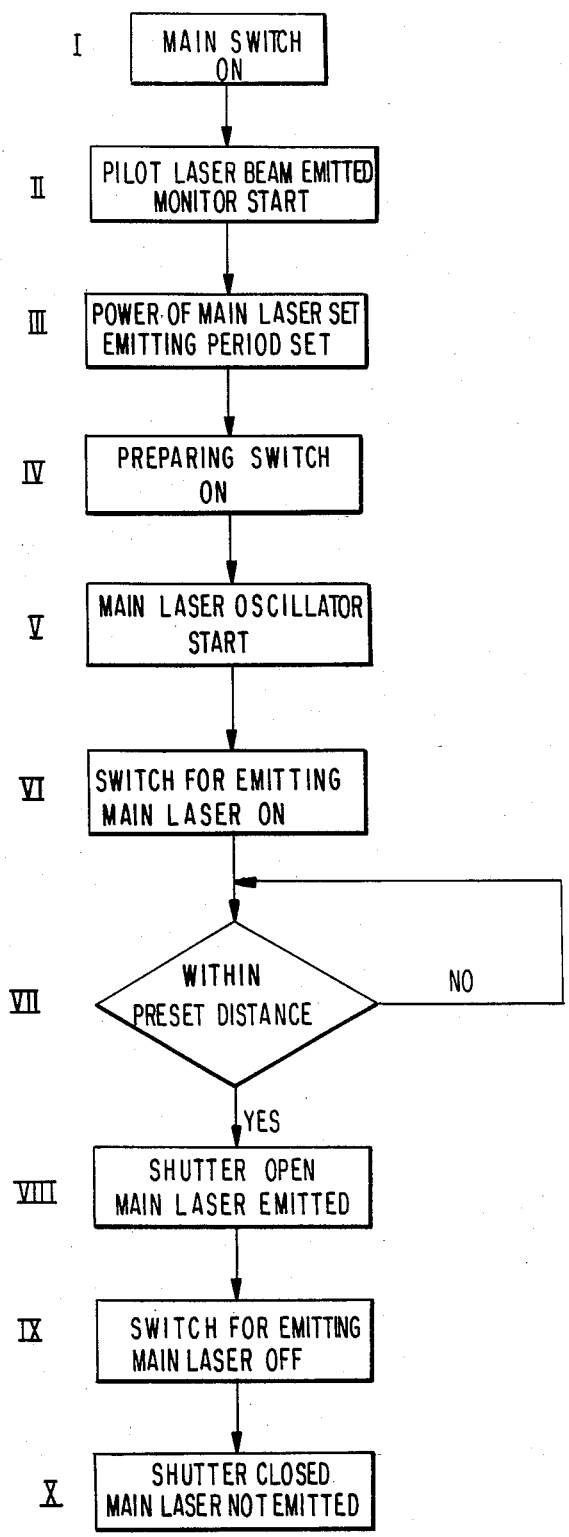
FIG. 11 is a flow chart showing the total operation of a general surgical laser system to which this invention is applicable.
Figure 12:
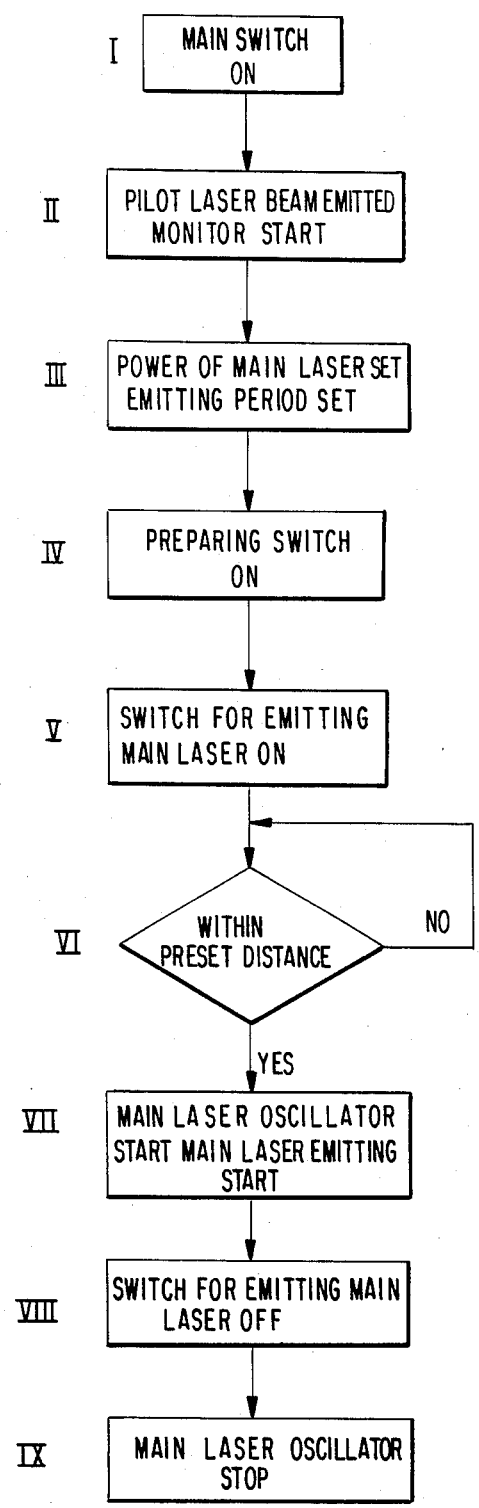
FIG. 12 is a similar flow chart showing the total operation of another type of general surgical laser system.

In the following embodiments of the invention the overall operation of the surgical laser system is similar to that shown in the flow charts of FIGS. 11 or 12, except for the step of detecting the distance between the handpiece and the target.

Figure 6A:
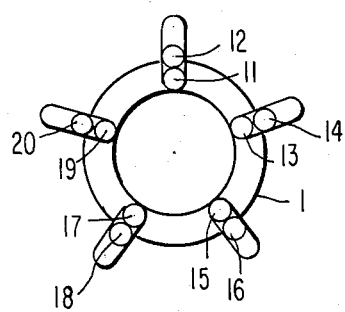
FIGS. 6(a) and 6(b) show end and elevation views, respectively, of a light detector arrangement according to an embodiment of this invention.
Figure 6B:
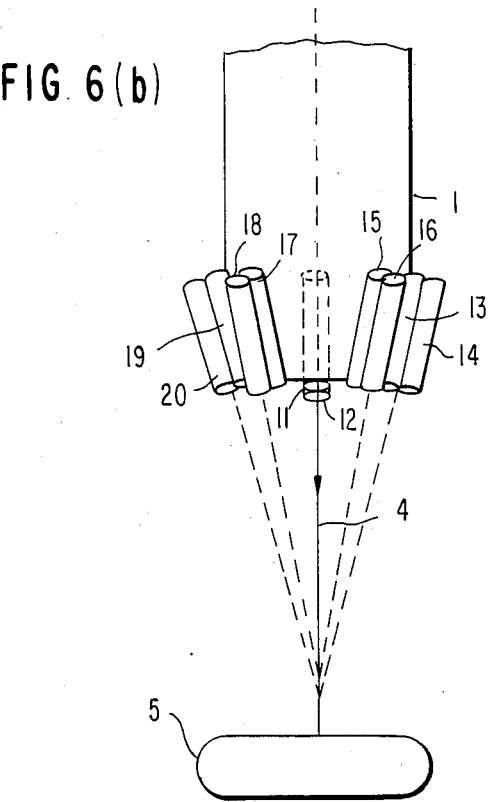

FIGS. 6(a) and 6(b) illustrate the end structure of a laser light emitting handpiece 1 according to the invention, comprising five pairs of angled light detectors 11 through 20 spaced around the handpiece tip circumference; FIG. 7 is a block diagram showing the entire laser light erroneous impingement protective device provided with an emitter handpiece structure as illustrated in FIGS. 6(a), (b). The pilot source laser beam 4 reflected from the target 5 is sensed by all five pairs of light detectors 11 through 20.

A pair of light detectors 11 and 12, for example, produce outputs corresponding to the received light, which are supplied to a distance measuring unit 21 such as a differential comparator. The latter produces an output A-B between the output A of the detector 11 and the output B of the detector 12. When A-B>0 the ON region is determined to exist for detectors 11, 12, which results in a "1" signal. Conversely, when A-B≦0 the OFF region is determined to exist for detectors 11, 12, and a "0" signal is produced by the measuring unit 21. Each of the distance measuring units 22-25 similarly produces a "1" or a "0" signal corresponding to the outputs of other associated pairs of light detectors.

The signals from the respective distance measuring units 21-25 are fed to an adder 26 for the addition of all of the signals. The summation output from the adder 26 is transmitted to a distance determining unit 27, where it is compared with a predetermined threshold (for instance, 2.5 by a majority decision), and said distance determining unit 27 indicates the ON region if the value of its output exceeds the threshold. Conversely, the distance determining unit indicates the OFF region if the output value from the adder 26 is less than the threshold.

If an ON region determination is made by the distance determining unit 27, when the handpiece switch 6 is turned on a laser beam control device 8 actuates a laser power source 10 so that a high powered main laser beam is emitted by the laser beam emitting device 9 at the handpiece. If, however, the distance determining unit 27 indicates the OFF region, the laser power source 10 will not be energized even though the switch 6 on the handpiece is turned on, whereby there is no emission of the high power laser beam.

Thus, if the same distance is set up in accordance with the respective pairs of light detectors, the same decision will result from the distance measuring unit even if no regular reflection components are received by any of the detectors. Further, if a sharp or regular reflection component is received by any one of the detectors, there would be a fear of error in any distance determination based only on the pair including said detectors, but such errors are reduced almost to zero when the distance determination is made by a majority decision based on the light received by five spaced pairs of detectors.

In addition, stable operation may also be provided for targets having rugged and varied surfaces by measuring the reflected light of the laser beam taken from five different directions. In this case, for instance, should a value of 3.5 be chosen as the decision threshold, the system would always function in a fail safe manner.

The described embodiment employs five pairs of light detectors, but obviously any other number of pairs more than three may be used. Further, instead of the adder 26, a logic circuit or microcomputer may be used.

Figure 8:
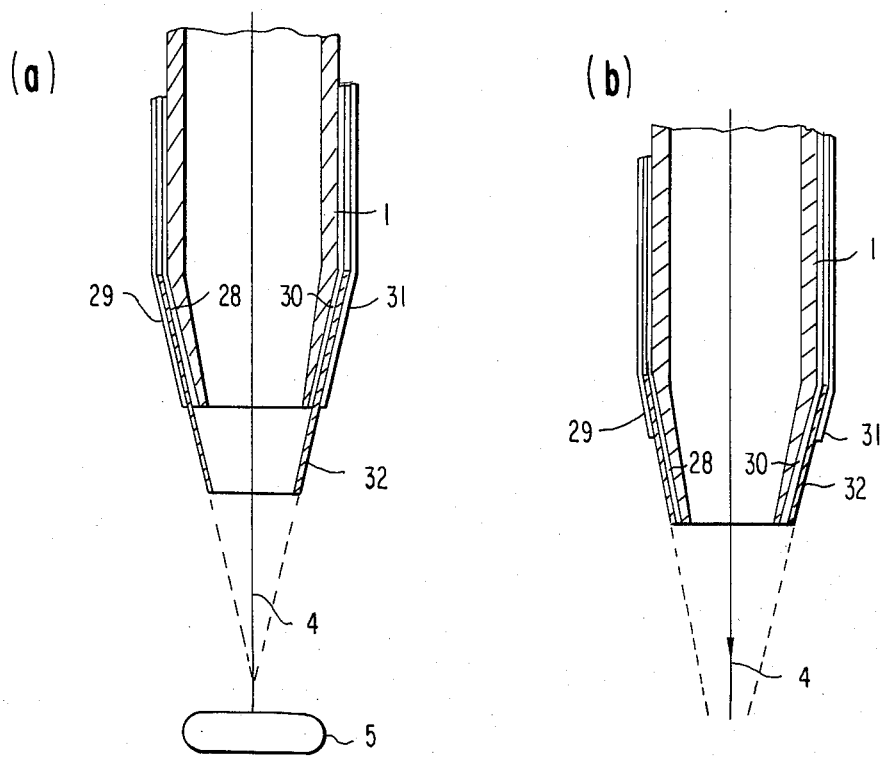

The light detectors have only been described as single units attached to the handpiece, but a similar result can also be achieved with a different arrangement wherein the light detectors are connected to the ends of similarly oriented optical fibers. In this event, for the provision of directivity, a directional plate 32 or the like may be placed between the inner fibers 28, 30 and the outer fibers 29, 31, as shown in FIGS. 8(a) and 8(b). By the use of such fibers, a lowering of the surgical efficiency caused by the attachment of the detectors may be prevented and the outer appearance of the whole unit can be improved.

Figure 1:
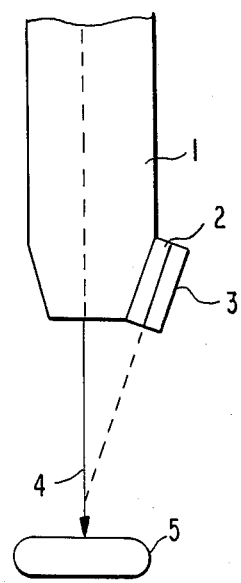
FIG. 1 is a schematic view showing a distance measuring method of a conventional laser light erroneous impingement protective device.
Figure 2:
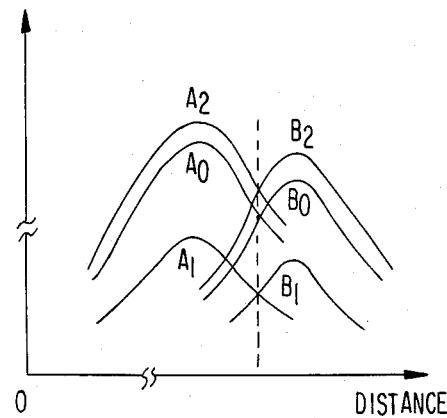
FIG. 2 shows representative distance-output characteristics of the light detectors of the device.
Figure 3:
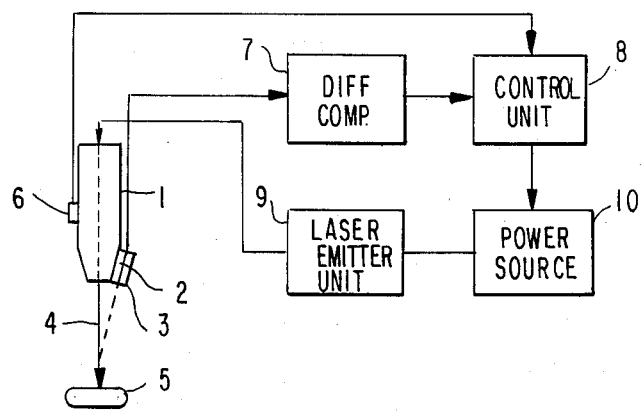
FIG. 3 shows a block diagram of the conventional protective device.
Figure 4:
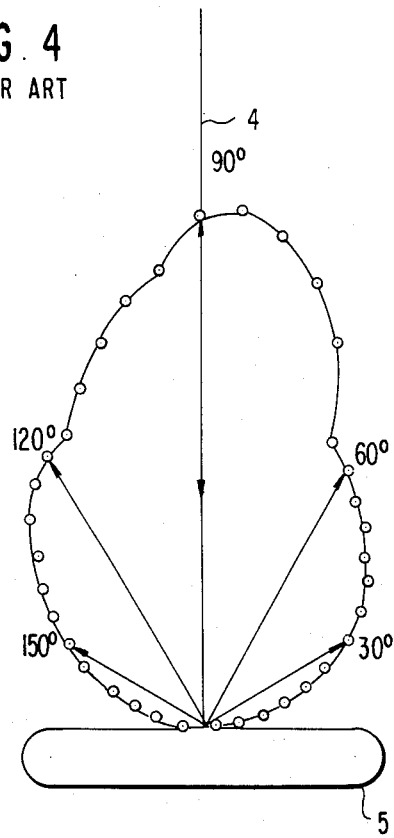
FIG. 4 represents a reflection distribution characteristic for a ham.
Figure 5:
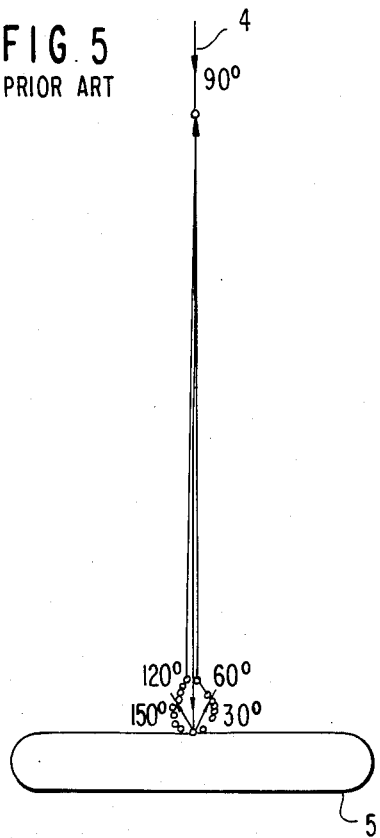
FIG. 5 shows a reflection distribution characteristic for a beef liver.

The output characteristics as shown in FIG. 2 may be obtained by an arrangement such that the light detectors are positioned in the direction of the periphery of the laser light emitting end to give each of them a different directivity. Though the protective device has been described for a surgical laser, the system can also be applied to a processing instrument utilizing a laser beam, for instance. Furthermore, instead of the provision of a visible pilot laser beam, another embodiment can consist in the use of the main laser beam for surgical purposes and the main laser beam for finishing purposes in conjunction with the pilot laser beam of the present system, whereby only one laser oscillator is needed as the source for both the pilot beam and the main beam. In these cases, means are required to suspend the emission of the main laser beam for an OFF distance decision by the light detectors; for example, it would be sufficient to screen the main laser beam with a shutter plate.

Figure 9:
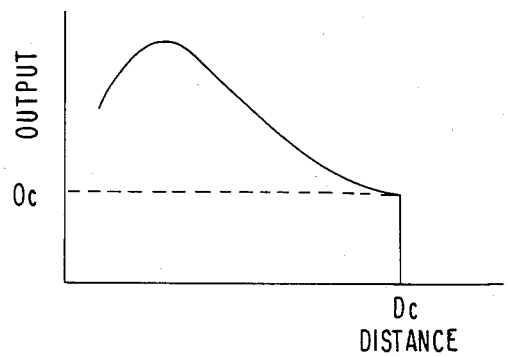
FIG. 9 represents distance-output characteristics of the ideal type of light detector for use in the establishment of distance.
Figure 10:
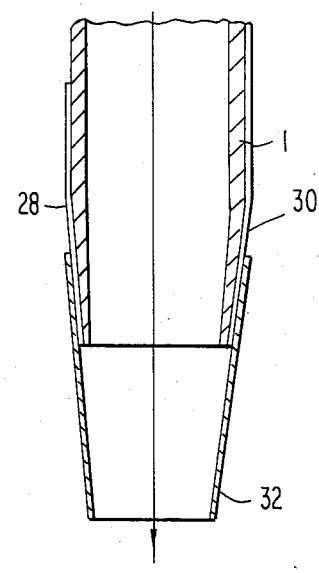
FIG. 10 is a sectional side view of a detector which has a characteristic similar to that shown in FIG. 9.

In the embodiments described above a plurality of pairs of differential light detectors are utilized. Instead, plural light detectors which have ideal distance-output characteristics as shown in FIG. 9 can be used to produce similarly good results if they are attached to the handpiece in such a way as to surround it. Such a detector is shown in FIG. 10. In a specific example where the diameters of the optical fibers 28, 30 are 0.1 mm, the distance between the ends of the fibers and the end of the directive plate 32 is 20 mm, the diameters of the directive plate are 19.6 mm at the ends of the optical fibers and 14.5 mm at the end of the directive plate, and the diameter of a visible pilot laser beam is 0.2 mm, ON-OFF controlling could be performed at a preset distance of 70±5 mm.

The reason why the distance-output characteristic shown in FIG. 9 is ideal will be briefly explained. In general, output distance characteristics having a critical point where the output changes sharply or abruptly are preferable because this enables a precise distance determination. It is extremely difficult to predetermine or detect distance correctly without such a critical point in the response curve when the detector is not of the differential type.

Surgical operations are usually performed under circumstances where lamps emitting intense light are provided, whereby it is necessary to avoid undesirable effects from such lamps. A system such as shown in FIG. 13 can effectively distinguish a pilot beam from the light from the operating room lamps.

Figure 13:
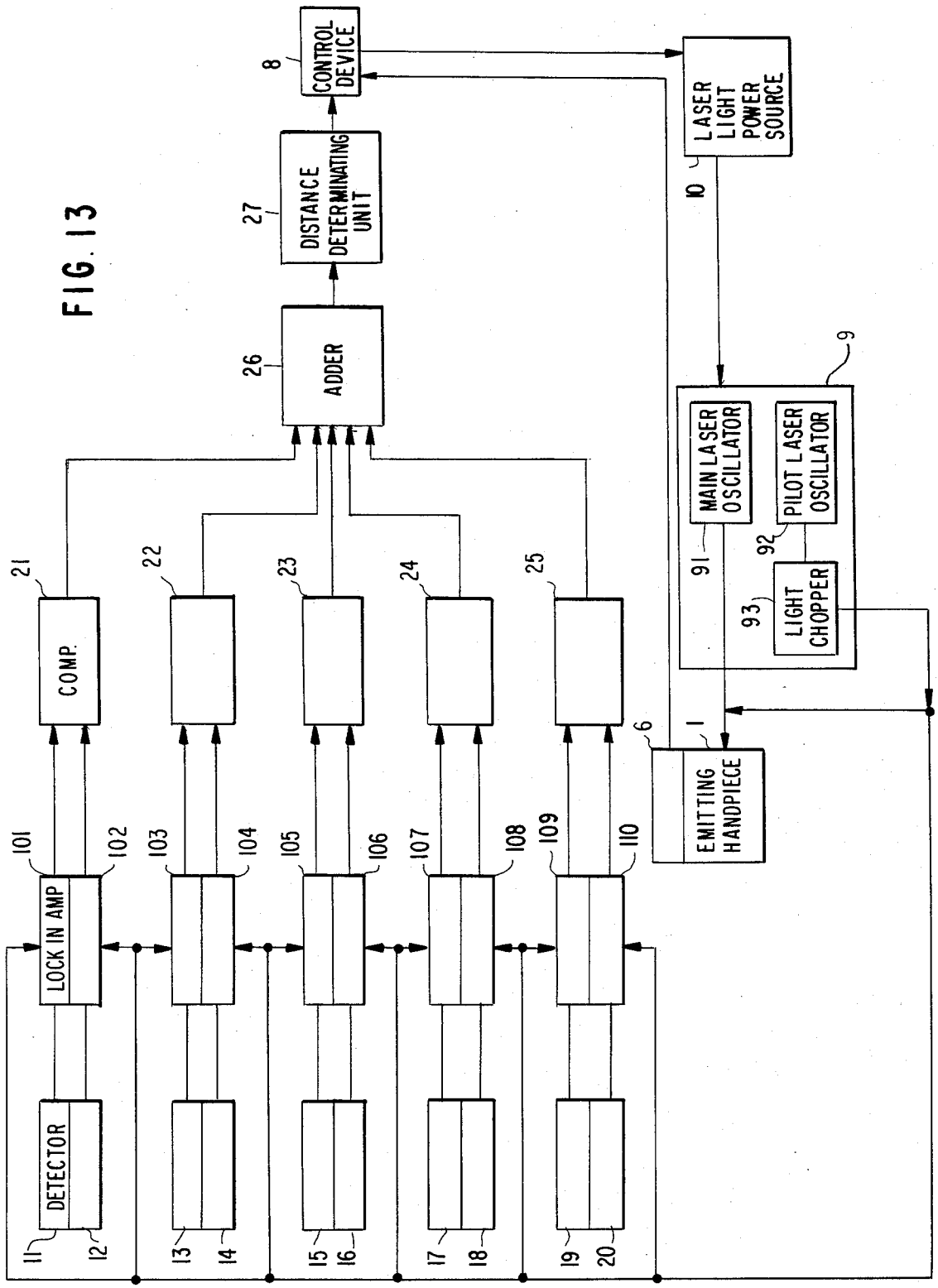
FIG. 13 is a block diagram showing another embodiment of this invention.

In FIG. 13 a light chopper 93 provided at the outlet side of the pilot laser oscillator 92 chops the pilot beam which is supplied to both the handpiece 1 and to lock-in amplifiers 101-110 connected between the detectors 11-20 and the comparators 21-25. With such an arrangement the lock-in amplifiers 101-110 detect only light whose frequency is the same as that of the pilot beam, thereby eliminating any effects of the ambient light.

Instead of the lock-in amplifiers, filters provided at the inputs of the comparators are also applicable.

What is claimed is:
1. A laser light erroneous impingement protective device, comprising: a surgical laser handpiece (1) including an end portion for emitting both a surgical laser beam and a visible pilot lase beam (4), a plurality of n pairs of light detecting means (11-20) equally circumferentially spaced around said end portion of the handpiece for detecting pilot beam light directly reflected from a target to which a pilot laser beam is applied and for generating electrical outputs proportional to the magnitude of such reflected light, a plurality of distance measuring units (21-25) each including a differential comparator responsive to the outputs of one of the detecting means pairs for generating a binary "0" or "1" logic signal in response to the relative magnitude of the detecting means pair outputs indicative of the distance between said end portion of said laser emitting means and the target, an individual one of said distance measuring units being provided for each of said plurality of pairs of light detecting means, an adder (26) for summing the binary logic signal outputs of each of the differential comparators, a majority decision distance determing unit (27) for making a final determination of an acceptable distance from the end portion of the handpiece to the target on the basis of the adder output and a predetermined threshold value less than n, and means for controlling the application of the surgical laser beam to the target in response to the output of the distance determining unit to thereby reduce activation errors due to the reflective characteristics and contours of the target surface and the angle of the handpiece.

2. Device as claimed in claim 1, wherein each of the plurality of pairs of light detecting means comprises optical fibers disposed on the periphery of said end portion of the handpiece and light detectors coupled to outputs of said optical fibers and disposed remote from said end portion.

3. Device as claimed in claim 1, further comprising a light chopper for chopping the pilot beam emitted at said end portion of said handpiece, and wherein said measuring units include lock-in amplifiers responsive to the chopped pilot beam for eliminating any undesired responses to ambient light.

* * * * *